United States Patent

Hauth

[11] 4,219,556
[45] Aug. 26, 1980

[54] SUBSTITUTED-8-PHENYLAMINO ERGOLINES

[75] Inventor: Hartmut Hauth, Riehen, Switzerland

[73] Assignee: Sandoz Ltd., Basel, Switzerland

[21] Appl. No.: 939,105

[22] Filed: Sep. 1, 1978

[30] Foreign Application Priority Data

Sep. 2, 1977 [CH] Switzerland ............... 10732/77

[51] Int. Cl.² ............... C07D 457/12; A61K 31/48
[52] U.S. Cl. ............................. 424/261; 546/68
[58] Field of Search ............... 424/261, 226; 260/285.5; 546/68

[56] References Cited

U.S. PATENT DOCUMENTS

| 2,997,470 | 8/1961 | Pioch | 424/261 |
|---|---|---|---|
| 3,185,695 | 5/1965 | Bernardi et al. | 546/68 |
| 4,004,011 | 1/1977 | Hauth et al. | 424/261 |

Primary Examiner—Mary C. Lee
Attorney, Agent, or Firm—Gerald D. Sharkin; Robert S. Honor; Thomas O. McGovern

[57] ABSTRACT

Compounds of formula I

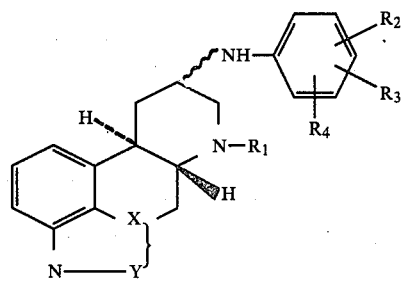

wherein
$R_1$ is hydrogen or lower alkyl,
$R_2$, $R_3$ and $R_4$ are, independently, hydrogen, halogen lower alkyl, lower alkoxy or $CONR_5R_6$ wherein $R_5$ and $R_6$ are, independently, hydrogen or lower alkyl, and $\widehat{xy}$ is $-CH_2-CH=$ or $-CH=C=$.

are useful as central dopaminergic agents and prolactin secretion inhibitors.

10 Claims, No Drawings

SUBSTITUTED-8-PHENYLAMINO ERGOLINES

This invention relates to ergoline derivatives, processes for their production and pharmaceutical compositions containing them.

The present invention provides a compound of formula I

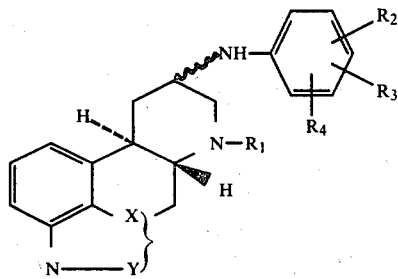

wherein
R₁ is hydrogen or lower alkyl,
R₂, R₃ and R₄ are, independently, hydrogen, halogen, lower alkyl, lower alkoxy or CONR₅R₆ wherein R₅ and R₆ are, independently, hydrogen or lower alkyl, and $\widehat{x\,y}$ is —CH₂—CH= or —CH=C=.

The present invention provides a process for the production of a compound of formula I as defined above which comprises reacting a compound of formula II

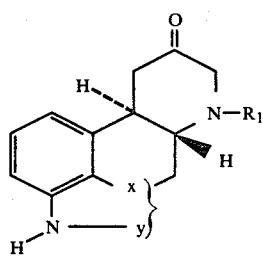

wherein R₁ and $\widehat{x\,y}$ are as defined above, in the presence of an amine of formula III

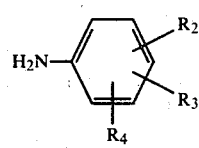

wherein R₂, R₃ and R₄ are as defined above, under reductive conditions, and from the resulting isomeric mixture isolating a compound of formula Ia

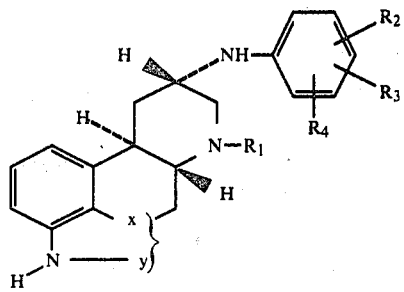

or a compound of formula Ib

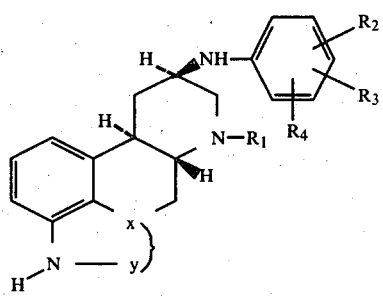

wherein R₁ to R₄ and $\widehat{x\,y}$ are as defined above.

In formula I, the alkyl and alkoxy groups have preferably 1 to 4 carbon atoms, especially 2 or 1 carbon atoms. Halogen means fluorine, chlorine or bromine. R₁ is preferably lower alkyl, preferably methyl. R₂ is preferably in the para position. R₂ is preferably alkoxy or halogen. R₃ and R₄ are conveniently hydrogen. $\widehat{x\,y}$ is conveniently —CH=C=. When $\widehat{x\,y}$ is —CH₂—CH= the hydrogen in position 3 conveniently has the β-configuration.

The above-mentioned process is conveniently effected in analogous manner to known reactions. Preferably catalytic hydrogenation in the presence of an noble metal catalyst, e.g. palladium on active charcoal, is used for the reductive conditions. Preferably acetic acid is present as solvent and the reaction is effected under normal atmospheric conditions.

To separate the components of the resultant isomer mixture, known methods for analogous separations may be used, e.g. chromatography using an appropriate solvent mixture, e.g. CH₂Cl₂/CH₃OH.

Free base forms of the compounds of formula I may be converted in conventional manner into acid addition salt forms, and vice versa. Suitable acids for salt formation include maleic acid and hydrochloric acid.

The starting materials are either known or may be made in conventional manner.

In the following examples all temperatures are in degrees Centigrade and are uncorrected.

EXAMPLE 1:
8-(4-ethoxyphenyl)amino-6-methylergoline

A solution of 17.8 g 6-methyl-8-oxo-ergoline in 800 ml acetic acid is slowly added over 8 hours to a mixture of 17.8 g 10% (by weight) palladium on charcoal and 10.3 g 4-ethoxyaniline in 300 ml acetic acid with simultaneous hydrogenation using normal atmospheric conditions. The catalyst is filtered off and the filtrate evaporated in a vacuum. The residue is taken up in CH₂Cl₂ containing 15% (by volume) isopropanol and washed with ice-cold ammonia and water. The organic phase is then dried, and evaporated in a vacuum. The residue is chromatographed on an 80-fold quantity of silicagel using $CH_2Cl_2$; as solvent, containing increasing amounts of $CH_3OH$. Elution with $CH_2Cl_2+2\%$ $CH_3OH$ gives an isomer of formula Ia:

(1a) (5R, 8S, 10S)-8-(4-ethoxyphenyl)amino-6-methylergoline;hydrogen maleate:
m.p. 219°-22°
$[\alpha]_D^{20} = -25°$ (c=0.48; 50% EtOH)

On further elution with $CH_2Cl_2+4\%$ $CH_3OH$ a compound of formula Ib is obtained:

(1b) (5R, 8R, 10S)-8-(4-ethoxyphenyl)amino-6-methylergoline
Free base m.p.>272° (decomp)
$[\alpha]_D^{20} \times -55°$ (c=0.5; Pyridine)

In analogous manner to example 1 the following compounds may be obtained:

(2) (5R, 8S, 10S)-8-(4-Fluorophenyl)amino-6-methylergoline Dihydrochloride:
m.p. 229° (decomp)
$[\alpha]_D^{20} = -27.4°$ (c=0.5 in 50% EtOH)

(2b) (5R, 8R, 10S)-8-(4-Fluorophenyl)amino-6-methylergoline Hydrogen maleate:
m.p. 229° (decomp)
$[\alpha]_D^{20} = -46°$ (c=0.5 in EtOH/H_2O 1:1)

(3a) (5R, 8S, 10S)-8-(3-N,N-dimethylcarboxamidophenyl) amino-6-methylergoline Hydrogen maleate:
m.p. 216°-218°
$[\alpha]_D^{20} = -40°$ (c=0.5; 50% EtOH)

(3b) (5R, 8R, 10S)-8-(3-N,N-dimethylcarboxamidophenyl) amino-6-methylergoline Hydrogen maleate:
m.p. 228°-230°
$[\alpha]_D^{20} = -36°$ (c=0.5; 50% EtOH)

(4a) (5R, 8S, 10S)-8-(3-chloro-5-ethylphenyl)amino-2,3β-dihydroergoline.

(4b) (5R, 8R, 10S)-8-(3-chloro-5-ethylphenyl)amino-2,3β-diihydroergoline.

(5a) (5R, 8S, 10S)-8-(2-carboxamido-3-N-ethyl carboxyamido-5-bromophenyl)aminoergoline.

(5b) (5R, 8R, 10S)-8-(2-carboxamido-3-N-ethylcarboxyamido-5-bromophenyl)aminoergoline.

The compounds of formula I exhibit pharmacological activity in animals. In particular, the compounds of formula I exhibit central dopaminergic stimulant activity, as indicated by standard tests, for example according to the principles of U. Ungerstedt, Acta Physiol. Scand. Suppl., (1971) 367, 69-93, by an induction of contralateral turning in rats lesioned unilaterally in the substantia nigra by 6-hydroxydopamine on s.c. administration of from about 1 to about 40 mg/kg.

The compounds are therefore useful as anti-Parkinson agents.

Additionally, the compounds, especially the compounds of formula Ia, exhibit prolactin secretion inhibition activity, for example, in rats by an inhibition of ovum implantation as follows:

The compound under investigation is administered to female rats 5 days after coitus and shown to be sperm positive according to the vaginal smear test. The rats are sacrificed on day 12 and their uteri are examined by means of the Salewski reaction for proof that the nidation process has been interrupted [Arch.exp. Path. Pharm.247, 367 (1967)].

The compounds are administered s.c. at from about 1 to about 10 mg/kg animal body weight.

The compounds are therefore useful as prolactin secretion inhibiting agents.

For the above-mentioned uses the dosage will, of course, vary depending on the compound employed, mode of administration and therapy desired. However, in general, satisfactory results are obtained when administered at a daily dosage of from 0.01 mg to about 15 mg per kg animal body weight, conveniently given in divided doses 2 to 4 times a day or in sustained release form. For the larger mammal, the total daily dosage is in the range from about 0.5 to about 50 mg, and dosage forms suitable for oral administration comprise from about 0.1 mg to about 25 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms.

The present invention also provides a pharmaceutical composition comprising a compound of formula I, in free base or in pharmaceutically acceptable acid addition salt form, in association with a pharmaceutical carrier or diluent. Such compositions may be formulated in conventional manner, so as to be, for example, a solution or a tablet.

The Example 1 compound exhibits particularly interesting activity. In a group of compounds $R_2$ is alkoxy, $CONR_5R_6$ or halogen in the 3 or 4 position and $R_3$ and $R_4$ are each hydrogen.

What we claim is:

1. A compound of formula I wherein
$R_1$ is hydrogen or lower alkyl,
$R_2$, $R_3$ and $R_4$ are, independently, hydrogen, halogen lower alkyl, lower alkoxy or $CONR_5R_6$ wherein $R_5$ and $R_6$ are, independently, hydrogen or lower alkyl, and $\widehat{x\,y}$ is $-CH_2-CH=$ or $-CH=C=$,
or a pharmaceutically acceptable acid addition salt thereof.

2. A compound of claim 1 wherein $R_2$ is alkoxy, $CONR_5R_6$ or halogen in the 3 or 4 position and $R_3$ and $R_4$ are each hydrogen.

3. The compound of claim 1 which is (5R,8S,10S)-8-(4-ethoxyphenyl)amino-6-methylergoline.

4. A pharmaceutical composition useful in treating Morbus Parkinson or inhibiting prolactin secretion comprising a therapeutically effective amount of a compound of claim 1 in association with a pharmaceutical carrier or diluent.

5. A method of treating Morbus Parkinson or inhibiting prolactin in animals which comprises administering a therapeutically effective amount of a compound of claim 1 to an animal in need of such treatment.

6. The compound of claim 1 which is (5R, 8R, 10S)-8-(4-ethoxyphenyl)amino-6-methylergoline.

7. The compound of claim 1 which is (5R, 8S, 10S)-8-(4-fluorophenyl)amino-6-methylergoline.

8. The compound of claim 1 which is (5R, 8R, 10S)-8-(4-fluorophenyl)amino-6-methylergoline.

9. The compound of claim 1 which is (5R, 8S, 10S)-8-(3-N,N-dimethylcarboxamidophenyl)amino-6-methylergoline.

10. The compound of claim 1 which is (5R, 8R, 10S)-8-(3-N,N-dimethylcarboxamidophenyl)amino-6-methylergoline.

* * * * *

UNITED STATES PATENT AND TRADEMARK OFFICE
CERTIFICATE OF CORRECTION

PATENT NO. : 4,219,556  Page 1 of 2
DATED : August 26, 1980
INVENTOR(S) : Hartmut Hauth It is certified that error appears in the above—identified patent and that said Letters Patent is hereby corrected as shown below:

On The Title Page,

In the "Abstract", delete the structural formula and insert in its place

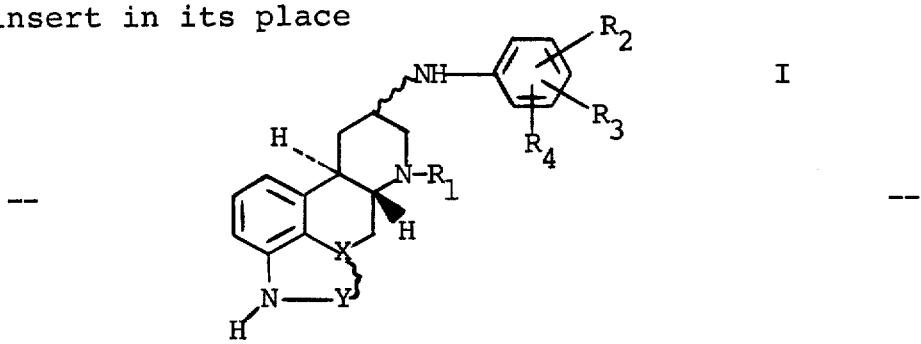

-- --

UNITED STATES PATENT AND TRADEMARK OFFICE
CERTIFICATE OF CORRECTION

PATENT NO. : 4,219,556

DATED : August 26, 1980

INVENTOR(S) : Hartmut Hauth

It is certified that error appears in the above—identified patent and that said Letters Patent is hereby corrected as shown below:

Column 4, Claim 1, delete the structural formula and insert in its place

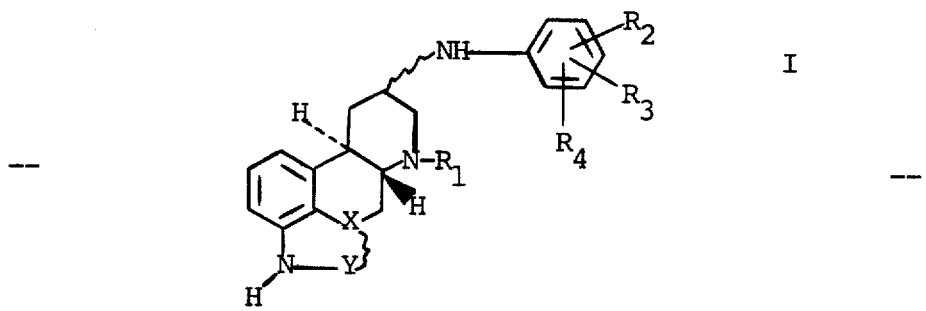

Signed and Sealed this

Twenty-second Day of June 1982

[SEAL]

Attest:

*Attesting Officer*

GERALD J. MOSSINGHOFF

*Commissioner of Patents and Trademarks*